(12) United States Patent
Biffi et al.

(10) Patent No.: US 10,881,703 B2
(45) Date of Patent: Jan. 5, 2021

(54) COMPOSITION FOR USE IN THE TREATMENT OF INTESTINAL ALTERATIONS

(71) Applicant: SOFAR S.P.A., Milan (IT)

(72) Inventors: Andrea Biffi, Milan (IT); Ruggero Rossi, Milan (IT); Walter Fiore, Milan (IT); Silvia Salamina, Milan (IT)

(73) Assignee: SOFAR S.p.A., Milan (IT)

( * ) Notice: Subject to any disclaimer, the term of this patent is extended or adjusted under 35 U.S.C. 154(b) by 15 days.

(21) Appl. No.: 16/465,511

(22) PCT Filed: Dec. 1, 2017

(86) PCT No.: PCT/IB2017/057580
§ 371 (c)(1),
(2) Date: May 30, 2019

(87) PCT Pub. No.: WO2018/100551
PCT Pub. Date: Jun. 7, 2018

(65) Prior Publication Data
US 2020/0061141 A1 Feb. 27, 2020

(30) Foreign Application Priority Data

Dec. 1, 2016 (IT) .............................. 10201612231

(51) Int. Cl.
| | | |
|---|---|---|
| *A61K 36/00* | (2006.01) | |
| *A61K 36/45* | (2006.01) | |
| *A61K 9/28* | (2006.01) | |
| *A61K 31/353* | (2006.01) | |

(52) U.S. Cl.
CPC .............. *A61K 36/45* (2013.01); *A61K 9/282* (2013.01); *A61K 9/2813* (2013.01); *A61K 9/2846* (2013.01); *A61K 9/2866* (2013.01); *A61K 31/353* (2013.01)

(58) Field of Classification Search
CPC ....................................................... A61K 36/00
USPC ........................................................... 424/725
See application file for complete search history.

(56) References Cited

FOREIGN PATENT DOCUMENTS

| DE | 20 2010 008 308 U1 | 11/2010 |
|---|---|---|
| WO | 01/80870 A2 | 11/2001 |
| WO | 2012/123491 A1 | 9/2012 |

OTHER PUBLICATIONS

International Search Report and Written Opinion, dated Mar. 2, 2018, for International Application No. PCT/IB2017/057580, 15 pages.
Lamiki et al., "Probiotics in Diverticular Disease of the Colon: an Open Label Study," *J. Gastrointestin. Liver Dis*. 19(1):31-36, 2010.
Topix, "Anyone try this approach to Diverticulosis," Diverticulitis Forum, Feb. 23, 2018, URL=http://m.topix.com/forum/health/diverticulitis/T44O0QL94E7AMQJ0B/p3, 6 pages.

*Primary Examiner* — Michael V Meller
(74) *Attorney, Agent, or Firm* — Seed IP Law Group LLP; Glenda A. Gertz

(57) ABSTRACT

The present invention relates to a composition which comprises a mixture which comprises or, alternatively, consists of an extract (a) of a fruit of at least one plant of the genus *Vaccinium* and at least one ingredient (b) acceptable for pharmaceutical or food use and the use thereof in the prevention and/or treatment of diverticular disease or of a pathology deriving therefrom or correlated thereto.

11 Claims, 13 Drawing Sheets

*E.coli* 2500X  *E.coli* 7500X

*E.coli* 750X (2 h)   *E.coli* 1000X (2 h)

*E.coli* 5000X (2 h) *E.coli* 10000X (2 h)

CRANBERRY + E.coli 1000X

CRANBERRY + E.coli 5000X

CRANBERRY + E.coli 10000X

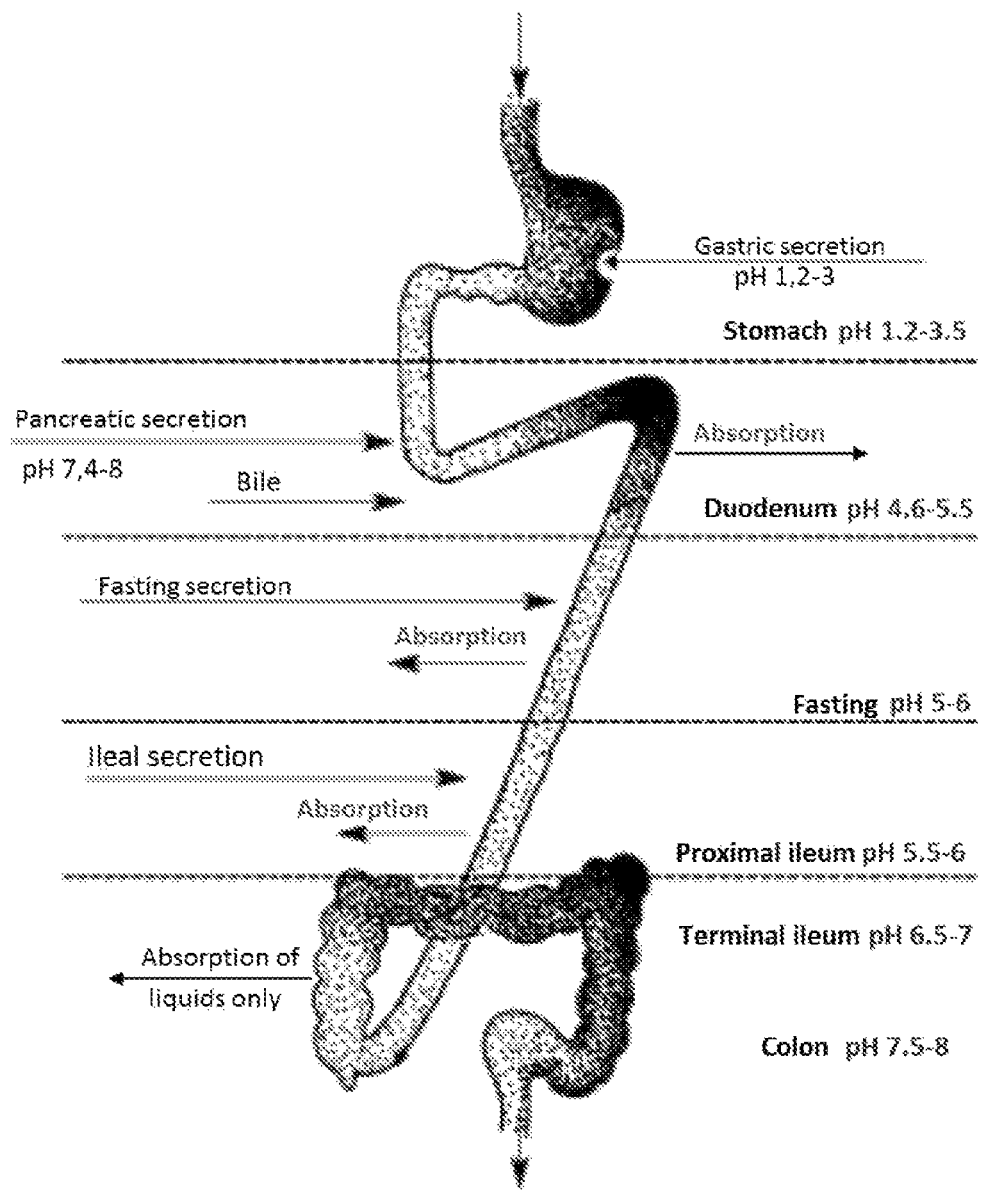
Figura 11

COMPOSITION FOR USE IN THE TREATMENT OF INTESTINAL ALTERATIONS

The present invention relates to a composition which comprises a mixture which comprises or, alternatively, consists of an extract (a) of a fruit of at least one plant of the genus *Vaccinium* and at least one ingredient (b) acceptable for pharmaceutical or food use and the use thereof in the prevention and/or treatment of diverticular disease or of a pathology deriving therefrom or correlated thereto.

The intestine represents the target organ of numerous inflammatory pathologies, which can be the cause of serious disorders and are often difficult for clinicians to manage.

Among them, a role of primary importance is occupied by:

inflammatory bowel disease (IBD).
pouchitis.
diverticular disease and diverticulitis.

Inflammatory bowel diseases (IBD) are characterised by the presence of a chronic inflammation of the mucosa of the intestine, which has an intermittent course and may cause severe complications. They include Crohn's disease (CD), ulcerative rectocolitis (URC) and so-called "indeterminate colitis" (IC).

The symptoms differ for the two most important pathologies of the group, namely, Crohn's disease (CD) and ulcerative rectocolitis (URC).

In the case of CD, the most frequent initial symptoms are diarrhoea and abdominal pain, localised above all in the right iliac fossa (corresponding to the last ileal loop, the most frequent site of disease).

URC, on the other hand, almost always manifests itself with bloody diarrhoea (containing bright red blood and mucus mixed with stools), associated with "tenesmus" (sensation of incomplete evacuation) and sometimes anaemia.

Both diseases can have periods of latency alternating with flare-ups of the inflammation. When the intestinal inflammation becomes acute again, constitutional symptoms such as fever, weight loss, asthenia and loss of appetite also appear. Over time CD can become complicated by the formation of stenosis (narrowing of the lumen of the affected portion of the intestine, which may ultimately lead to intestinal obstruction), fistulas (communications between the intestine and skin, or between abdominal organs) or abscesses.

So-called "indeterminate colitis"—IC, by contrast, is a relatively recently acquired disease, in which the phlogosis is limited to the colon, with histological, clinical, radiological and endoscopic characteristics such as to preclude a classification, as they can be ascribed neither to CD nor to URC; in 13-20% of the cases they represent initial forms of one of the two.

So-called "indeterminate colitis"—IC is generally characterised by: the presence of segmental lesions, extensive ulceration, possible involvement of the right colon—even though the distal colon (left colon) is more severely compromised—and the presence of inflammation extending over more than 50% of the mucosal surface, with the possible dilation of the colon associated with toxic megacolon.

In a large majority of cases (95%), the symptoms are characterised initially by diarrhoeal bowel movements at the start; there is a presence of bloody diarrhoea in 72% of cases and abdominal pain in 74%. A smaller percentage of patients present with weight loss (44%) and fever (26%).

Pouchitis is a non-specific inflammation of the ileal reservoir or pouch and is the most frequent long-term complication of the surgical intervention known as ileal pouch-anal anastomosis.

The etiology is still unknown and most likely multifactorial. Various pathogenetic hypotheses have been proposed, including faecal stasis and bacterial overgrowth, recurrence of URC and ischaemia of the pouch mucosa.

Pouchitis is clinically characterised by variable symptoms, which include an increase in the number of evacuations and the fluidity of the faeces, rectal bleeding, cramp-like abdominal pains, urgency and tenesmus, and sometimes incontinence and fever.

Colonic diverticulosis is the most frequent anatomical alteration of the colon, often detected during colonoscopy. It refers to the presence of structural modifications of the colon wall, and appears to be characterised by the presence of pouches called "diverticula"; it is distinct from inflammatory bowel disease (IBD) and pouchitis.

Diverticula are small protruding pouches that can form in the lining of the colon in points of relative weakness of the muscle layer of the wall.

The condition in which diverticula are detected, even if there are no symptoms linked to their presence, takes the name "diverticulosis". In practical terms, diverticulosis is a medical condition characterised by the presence of protrusions of the mucosa and sub-mucosa—defined as diverticula, precisely—along the wall of the hollow organs of the digestive system. They generally form in areas of relative weakness of the muscle layer ("Locus minoris resistentiae") of the colon (above all the sigmoid colon and rectum due to the higher pressures). Diverticulosis manifests itself without symptoms; if it becomes symptomatic, such as, for example, in the case of diverticulitis, one speaks of diverticular pathology or disease.

Diverticulosis is most common in Western countries, with a prevalence of 5% in the population aged between 30 and 39 years and 60% in the part of the population over 80 years of age.

Diverticula are more common in the lower part of the large intestine (or colon), called sigmoid colon.

It is believed that the development of colonic diverticula is the result of an increase in the intraluminal pressure of the colon. To be clear, the development of diverticula is a phenomenon that differs completely from inflammatory and/or autoimmune phenomena such as chronic inflammatory bowel disease (IBD), for example Crohn's disease and ulcerative colitis, and, based on our present knowledge, such pathologies have no connection with diverticulosis and the disorders associated therewith.

The presence of diverticula is a permanent anatomical alteration in the structure of the walls of the colon, which can remain asymptomatic or lead to the development of symptoms. It is estimated that about 20% of patients develop symptoms, in the presence of which the condition is defined as "diverticular disease" (DD).

Uncomplicated diverticular disease is not usually associated with specific symptoms. Diverticular disease is a common cause of significant bleeding from the colon.

A sub-type of DD is SUDD (symptomatic uncomplicated diverticular disease), in which persistent abdominal symptoms attributed to diverticula are present in the absence of macroscopically manifest colitis or diverticulitis.

Other symptoms are usually related to complications of diverticular disease, such as "diverticulitis", which is a macroscopic acute inflammation of the diverticula. Diverticulitis may be simple or complicated, depending on whether characteristics of complications such as abscesses, peritonitis, obstruction, fistulas or haemorrhaging are observed on computed tomography (CT) or not.

Diverticulitis can cause abdominal pain, shivers, fever and a change in bowel habits. The most intense symptoms are associated with serious complications such as perforation (a free break in the abdomen), abscesses (buildup of pus) or the formation of fistulas (an anomalous passage that is created between the colon and another organ or with the skin following a perforation of the diverticulum).

The underlying pathological mechanisms that cause the formation of colonic diverticula (diverticulosis) still remain unclear. Without wishing to be limited by this theory, such formations are probably the result of complex interactions between diet, intestinal microbiota, genetic factors, motility of the colon and microscopic inflammation.

Although it has not been proven, the currently prevailing theory is that a diet with a low fibre intake is among the causes of diverticular disease. The disease was noted in the early years of the 20th century in the United States, at a time when certain foods were introduced into the American diet, considerably reducing the fibre intake of the American population.

Diverticular disease is common in industrialised countries and, in particular, in the United States, England and Australia where diets with a low fibre intake are prevalent. The disease is rare, by contrast, in Asia and Africa, where the majority of people have a high dietary intake of fibre.

Fibre is found in fruit, vegetables and unrefined (whole) grains that the body is unable to digest completely. Some fibres, called soluble fibres, dissolve easily in water, creating a soft gelatinous material in the intestine, whereas insoluble fibre passes through the intestine almost intact. Both types of fibre help to prevent constipation, with soft stools that are easily expelled.

Constipation manifests itself with the need for considerable effort in order to defecate; the effort may cause an increase in pressure in the colon, and this in turn may cause the lining of the colon to swell through the weak points in the wall of the colon, which may lead to the formation of pouches, i.e. diverticula.

Lack of physical exercise can increase the risk of the formation of diverticula, even though his aspect has not yet been considered determinant.

At present, bowel rest, a specific diet with a low fibre content and wide-spectrum antibiotics, often associated with an antispastic drug, are prescribed as medical therapy for diverticular disease and/or diverticulitis. The use of non-steroidal anti-inflammatory drugs (NSAIDs) and corticosteroids is not common, because these drugs can facilitate a perforation in proximity to diverticulum. In the most complicated cases, such as, for example, peritonitis, abscesses and fistulas, an emergency resection, with or without anastomosis, may be necessary.

At present, there is no available treatment capable of preventing the formation of diverticula or of inducing a reduction therein or of effectively preventing diverticulitis in individuals with diverticular disease or diverticulosis.

BRIEF DESCRIPTION OF THE DRAWINGS:

FIG. 11 depicts an illustration of the gastrointestinal tract.

Figure 1:
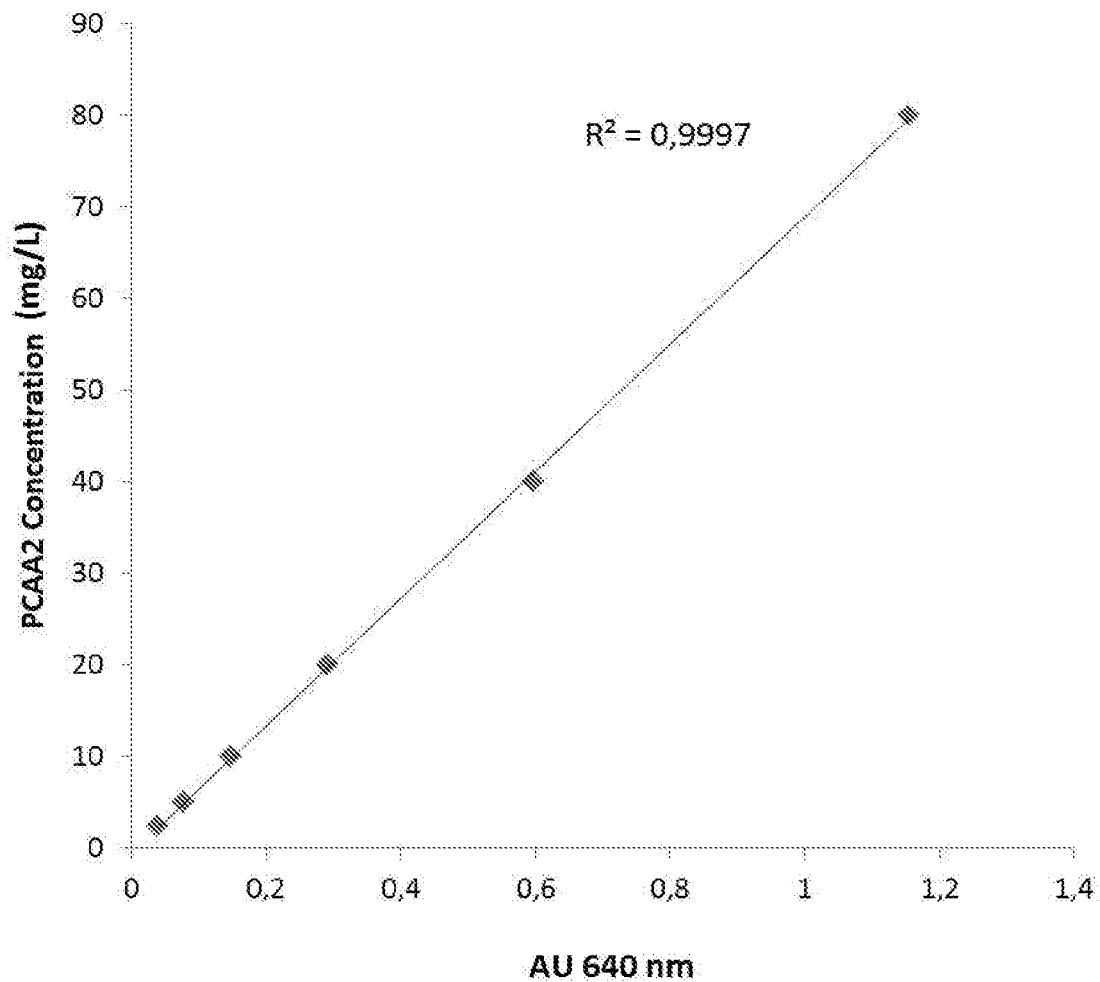
FIG. 1 depicts a calibration curve for the dissolution test.

In order to respond to the above-mentioned limits of the prior art, the present invention provides a new composition for oral administration, which comprises an extract deriving from plants of the genus *Vaccinium* for use in the prevention or treatment of diverticulosis in the colon, or in the portion of the sigmoid colon and rectum, and of pathologies or diseases linked to the presence of diverticula, such as diverticular disease, SUDD (symptomatic uncomplicated diverticular disease) and diverticulitis in the colon, or in the portion of the sigmoid colon and rectum.

The present invention relates to a composition for oral administration (CR) which comprises or, alternatively, consists of:

(i) a core comprising, or, alternatively, consisting of an extract (a) of at least one plant of the genus *Vaccinium* and at least one ingredient or excipient (b) acceptable for pharmaceutical or food use;

(ii) a gastro-resistant layer external to the core (i) and which completely coats said core (i) and which comprises at least one ingredient or excipient (c) acceptable for pharmaceutical or food use, wherein said gastro-resistant layer (ii) is capable of enabling the release of the extract (a) in the mucosa of the intestine; it is preferably capable of enabling the release of the extract (a) in the colon.

The present invention further relates to a composition for oral administration (CR) which comprises or, alternatively, consists of:

(i) a core comprising, or, alternatively, consisting of an extract (a) of at least one plant of the genus *Vaccinium* and at least one ingredient or excipient (b) acceptable for pharmaceutical or food use;

(ii) a gastro-resistant layer external to the core (i) and which completely coats said core (i) and which comprises at least one ingredient or excipient (c) acceptable for pharmaceutical or food use, wherein said gastro-resistant layer (ii) is capable of enabling the release of the extract (a) in the colon.

The present invention further relates to a composition for oral administration (CR) which comprises or, alternatively, consists of:

(i) a core comprising, or, alternatively, consisting of an extract (a) of at least one plant of the genus *Vaccinium* and at least one ingredient or excipient (b) acceptable for pharmaceutical or food use;

(ii) a gastro-resistant layer external to the core (i), which completely coats said core (i) and which comprises at least one ingredient or excipient (c) acceptable for pharmaceutical or food use, wherein said gastro-resistant layer (ii) is capable of enabling the release of the extract (a) in the colon; wherein said composition is for use in the prevention and/or treatment of diverticulosis in the colon, or in the portion of the sigmoid colon and rectum, and of pathologies or diseases linked to the presence of diverticula, such as diverticular disease, SUDD (symptomatic uncomplicated diverticular disease) and diverticulitis in the colon, or in the portion of the sigmoid colon and rectum.

The composition (CR) of the present invention is gastro-protected and is in the solid form of a powder, granules, flakes, tablets, pills or capsules; it is preferably a gastro-protected monolithic tablet. In this case, the core (i) is represented by and coincides with the monolithic tablet.

The present invention relates to a composition (C) which comprises, or, alternatively, consists of:
an extract (a) of a fruit of at least one plant of the genus *Vaccinium*, and
at least one ingredient and/or excipient (b) acceptable for pharmaceutical or food use,
said composition being for use in the prevention and/or treatment of diverticulosis in the colon, or in the portion of the sigmoid colon and rectum, and of pathologies or diseases linked to the presence of diverticula, such as diverticular disease, SUDD (symptomatic uncomplicated diverticular disease) and diverticulitis in the colon, or in the portion of the sigmoid colon and rectum; preferably wherein said use comprises oral administration of (C).

It is also possible that the composition (C) in the solid form, for example, of a powder, granules, beads or microbeads, or flakes is contained inside a shell, for example a capsule or a softgel, of gastro-resistant material capable of breaking down at a pH above 6, preferably a pH comprised from 6.5 to 8, for example a pH of 7.5. In this case, the composition (C) contained in said capsule or a softgel still has valid use in the prevention and/or treatment of diverticulosis in the colon, or in the portion of the sigmoid colon and rectum, and of pathologies or diseases linked to the presence of diverticula, such as diverticular disease, SUDD (symptomatic uncomplicated diverticular disease) and diverticulitis in the colon, or in the portion of the sigmoid colon and rectum; preferably wherein said use comprises oral administration of (C).

Preferred embodiments will be illustrated below, with no intention of limiting their scope and content in any way.

Unless otherwise specified, the content of an ingredient in a composition refers to the percentage by weight of that ingredient relative to the total weight of the composition.

Unless otherwise specified, the indication that a composition "comprises" one or more components means that other components may be present in addition to the one or ones specifically named and the indication that a composition "consists" of given components means that the presence of other components is ruled out.

The composition (C) can consist of (a) and (b) or can comprise other ingredients or excipients in addition to (a) and (b).

By way of non-limiting example, said additional ingredients which can be present in the compositions (CR) and (C) of the present invention may be other active ingredients, such as:
Fibres (e.g. inulin, psyllium)
Enzymes (e.g. galactosidase and the like)
Anti-inflammatories (e.g. mesalazine and derivatives, beclometasone and similar active ingredients)
Antibiotics (e.g. rifaximin and similar active ingredients)
Substances with an absorbent action at the intestinal level and/or a carminative and/or oral anti-foaming action, to reduce the formation of intestinal gas (e.g. peppermint, simethicone and derivatives, activated carbon)
Antioxidants
Substances with an immunomodulating action
Short-chain fatty acids (SOFA, such as butyrate and derivatives)
Omega-3 polyunsaturated fatty acids
Probiotics or, alternatively: microorganisms in the form of a lysate or extract (paraprobiotics), metabolic bioproducts generated by microorganisms (postbiotics) and/or any other product derived therefrom.

Non-limiting examples of said microorganisms that can be present in the compositions (CR) and (C) of the present invention are: probiotic bacteria belonging to the genera *Lactobacillus, Bifidobacterium* and *Enterococcus* and yeast, preferably belonging to the genus *Saccharomyces*, taken individually or in various combinations.

In a preferred embodiment, the core (i) present in said composition (CR) or (C) further comprises mannitol and/or at least one active ingredient with an anti-inflammatory action selected from among a steroidal anti-inflammatory drug, a non-steroidal drug and a substance or mixture of substances of natural origin.

Figure 2:
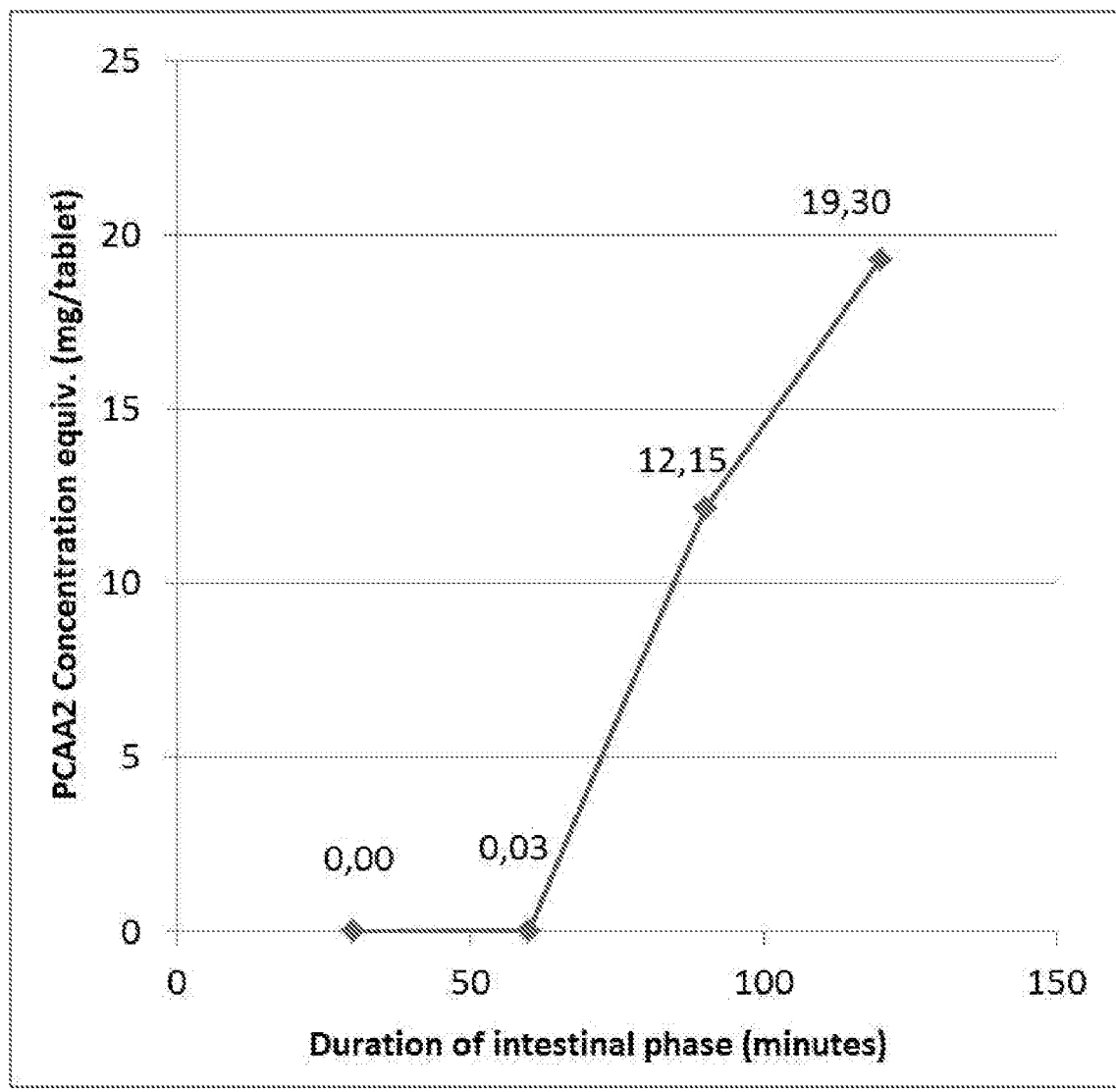
FIG. 2 depicts results of the dissolution test on the gastro-protected tablet according to the invention in the intestinal phase.

The present invention will also make reference to the following Figures:
FIG. 1: calibration curve for the dissolution test.
FIG. 2: results of the dissolution test on the gastro-protected tablet according to the invention in the intestinal phase.
FIG. 3-10: results of the study regarding the protective effectiveness on the intestinal mucosa (CacoGoblet): Colonisation with *E. Coli*.
FIG. 11: illustration of the gastrointestinal tract.

In the context of the present invention, the term "anti-inflammatory drug" is used in the common meaning of the term and indicates, as known to the person skilled in the art, any substance capable of reducing or eliminating an inflammatory process—in particular, but not limited to, damage to an individual's intestine.

In the composition (CR), as defined above, the gastro-resistant layer (ii) external to the core (i) comprises or, alternatively, consists of at least one substance selected from among Eudragard biotic E1207, a gastro-resistant polymer, such as poly(methyl acrylate-co-methyl methacrylate-co-methacrylic acid) 7:3:1 or another anionic methacrylic copolymer, triethyl citrate E1505, talcum, ethyl cellulose, anionic methacrylate copolymer and mixtures thereof, lac, sodium alginate and mixtures thereof, starch and modified starches, oleic acid, stearic acid and medium-chain triglycerides.

Preferred forms of the gastro-resistant layer (ii) external to the core (i) comprise or, alternatively, consist of:
a gastro-resistant polymer, such as poly(methyl acrylate-co-methyl methacrylate-co-methacrylic acid) 7:3:1 or another anionic methacrylate copolymer: from 5 to 50 mg; 10 to 35 mg; 18-25 mg;

Triethyl citrate E1505: from 0.1 to 5 mg; 0.3 to 3 mg; 0.5-2 mg;
Talcum: from 1 to 30 mg; 3 to 20 mg; 5-15 mg; or alternatively:
Ethyl cellulose: from 5 to 15 mg; 8 to 12 mg; 9.97 mg;
Sodium alginate: from 5 to 15 mg; 8 to 12 mg; 9.30 mg;
Ammonium hydroxide: from 0.5 to 4 mg; 1.5 to 3 mg; 2.34 mg;
Medium-chain triglycerides: from 0.5 to 5 mg; 1.5 to 3 mg; 2.12 mg;
Oleic acid: from 0.5 to 3 mg; 1 to 2 mg; 1.17 mg;
Purified stearic acid: from 0.01 to 0.5 mg; 0.05 to 0.3 mg; 0.1 mg; or alternatively:
ethyl cellulose: from 5 to 50 mg; 10 to 30 mg; 15-20 mg;
titanium dioxide: from 0.1 to 15 mg; 0.5 to 10 mg; 1-5 mg;
Sodium alginate: from 0.1 to 5 mg; 0.3 to 4 mg; 0.5-2 mg;
Oleic acid, stearic acid, Medium-chain triglycerides: each from 0.01 to 3 mg; between 0.05 and 1 mg.

Preferred forms of the gastro-resistant layer (ii) external to the core (i) comprise or, alternatively, consist of:
Eudragard® biotic E1207 (Evonik): for example 20.4 mg;
Triethyl citrate E1505: for example 1 mg;
Talcum: for example 10. 2 mg; or, alternatively:
Ethyl cellulose: for example 9.97 mg;
Sodium alginate: for example 9.30 mg;
Ammonium hydroxide: for example 2.34 mg;
Medium-chain triglycerides: for example 2.12 mg;
Oleic acid: for example 1.17 mg;
Purified stearic acid: for example 0.1 mg.

Said gastro-resistant layer (ii) external to the core (i) has the characteristic of breaking down and dissolving as a function of the pH value and/or time; advantageously said layer (ii) is formulated and prepared so as to be capable of breaking down and dissolving from a pH value of about 6.5 to a pH of about 8, preferably from a pH of about 7 to about 7.5 in a time comprised from 30 minutes to 120 minutes, preferably from 45 minutes to 90 minutes; for example at a temperature comprised from 30° C. to 40° C., preferably from 34° C. to 37° C.

After extended research and numerous experimental attempts, it was found that, advantageously, the use of one or more of said substances to form an external gastro-resistant layer makes it possible to obtain a composition (CR) for oral use, for example a tablet, capable of passing intact through the oral, esophageal and gastric tracts and enabling an initial breakdown of said (ii) gastro-resistant layer external to the core (i) starting from the terminal ileum at a pH of about 6.5-7, with or without an initial dissolution of the core (i) and a release of the extract (a), and the subsequent breakdown of said (ii) gastro-resistant layer external to the core (i) in the colon at a pH of about 7-8 with the dissolution of the core (i) and the release of the extract (a), mainly in the colon, at a pH of 7.5 (FIG. 11).

Experimental trials conducted demonstrate that the composition (CR) of the present invention, for example in the form of a monolithic tablet as per examples 1 and 2, remains intact within 2 hours at a pH of 1, whereas at a pH of 6 it remains intact within 1 hour. At a pH of 7.2, the gastro-resistant coating external to the core (i) of the composition (CR) begins to tear apart after about 30 minutes, whereas said coating is amply torn at a pH of 7.2 after 90 minutes; the film/coating opens and remaining inside it are small portions of the core (i) or in some cases powder deriving from the complete disintegration of the core (i).

As regards the release of said extract (a) present in said core (i), there is no release before the ileum up to a pH of 6.5. In the terminal ileum there is a release comprised from about 5% to about 20%, preferably from about 10% to about 15%. In the colon at a pH of about 7.5, for example a pH of about 7.2, there is a release comprised from about 80% to about 95%, preferably from about 85% to about 90%. Most of the release of said extract (a) occurs in the colon, which represents, precisely, the site where the diverticula are present and where the pathology or disease manifests itself. In this manner, the extract (a) released in the colon is capable of acting thanks to the presence also of PACs (proanthocyanidins), which are capable of performing an anti-inflammatory activity.

The composition (CR) according to the invention is in the form of a composition for a dietary supplement or a composition for a medical device or a composition for a food for special medical purposes or a pharmaceutical composition; all the compositions are in a pharmaceutical form for oral use.

In the context of the present invention, the term "medical device" is used with the meaning according to Italian Legislative Decree no. 46 of 24 Feb. 1997, which corresponds to the definition provided by the World Health Organization and available at the URL http://www.who.int/medical_devices/full_deffinition/en/, i.e. it indicates a substance or another product, used alone or in combination, intended by the manufacturer to be used, alone or in combination, for humans for the purposes of diagnosis, prevention, monitoring, treatment or alleviation of disease, which device does not achieve its primary intended action by pharmacological, immunological or metabolic means, in or on the human body, but which may be assisted in its intended function by such means.

In the composition (CR) as defined above, the extract (a) can be represented by fruits (more specifically berries), belonging to the genus *Vaccinium* and, optionally, also *Sambucus, Lycium, Euterpe* and combinations thereof. The extract (a) is preferably a dry extract.

In the composition (CR) as defined above, the extract (a) is preferably from the fruits of at least one plant of the genus *Vaccinium* and the subgenus *Oxycoccus*, such as *Vaccinium macrocarpon, Vaccinium oxycoccos*, or the subgenus *Vaccinium*, such as *Vaccinium arboreum, Vaccinium crassifolium, Vaccinium boreale, Vaccinium myrtillus* or mixtures thereof; preferably wherein the extract (a) is of the fruits of *Vaccinium macrocarpon* or of *Vaccinium oxycoccos* or a mixture thereof. More preferably still, the extract (a) comprises, or consists, of the fruits of *Vaccinium macrocarpon*. Advantageously, the extract (a) is a dry extract; in one embodiment it is a dry extract of cranberry, preferably containing PACs (proanthocyanidins) in a concentration of 5% to 30% by weight or volume, for example 10%, or 15%, or 20%, or 25%.

The American cranberry (*Vaccinium macrocarpon*) is a small evergreen shrub belonging to the family of the Ericaceae, which grows in boreal climate zones, in particular in North America and in some northern regions of Europe and Asia, and produces red fruits similar to berries, with a dense pulp and typically tart flavour.

In the past, among the Indians of North America, the cranberry was considered a sacred fruit and was used both as a food and as a treatment for kidney stones and various urinary tract problems.

Today the American cranberry is used worldwide for its countless beneficial properties, due fundamentally to the high content of proanthocyanidins (PACs), in particular A-type proanthocyanidins.

American cranberry extracts are used above all in the prevention and treatment of urinary tract disorders, but also as prevention against the adhesion of *Helicobacter pylori*, a bacterium that is often a cause of stomach and duodenal ulcers, to the walls of the stomach, or the adhesion of bacteria which populate the oral cavity and are responsible for the formation of plaque or the adhesion of potentially pathogenic bacteria such as *E. Coli* at an intestinal level.

European patent EP 2135616 B1 relates to the use of cranberries for the treatment of IBD and ulcerative colitis, which, as indicated above, are pathologies wholly distinct and different from those to which the present invention relates.

In the context of the present invention, the use of cranberry for the treatment of IBD and ulcerative colitis is excluded and thus not envisaged, just as the use of cranberry to prevent the adhesion of *Helicobacter pylori* to the walls of the stomach is not envisaged. Furthermore, the use of cranberry for the treatment of urinary tract infections (UTIs), such as cystitis (inflammation of the urinary bladder) or bacterial cystitis or non-bacterial cystitis, such as, for example, cystitis of the interstitial type, is excluded and thus not envisaged.

The inventor has found that the extract of fruits of the genus *Vaccinium*, in particular the American cranberry, is useful in the prevention and/or treatment, preferably by oral administration, of diverticulosis in the colon, or in the portion of the sigmoid colon and rectum, and/or of pathologies or diseases deriving from or linked to the presence of diverticula, such as diverticular disease, symptomatic uncomplicated diverticular disease (SUDD) and diverticulitis in the colon, or in the portion of the sigmoid colon and rectum.

In the composition (CR) according to the present invention the extract (a) preferably contains at least 10%, more preferably at least 15% or 20% or 30% and/or no more than 95% or 60% or 40% proanthocyanidins by weight out of the total weight of said extract (a), more preferably, but without limitation, of A-type proanthocyanidins. Proanthocyanidins (PACs) are oligomers and polymers of flavan-3-ols, which belong to the family of the flavonoids and can be quantified, for example, with the "BL-DMAC" method of Prior, R. L. et al. *J. Sci Food Agric* 2010, 90(9), 1473-8, or equivalent methods. Said extract (a) is preferably a dry extract; more preferably still, it is a dry extract of cranberry.

The composition (CR) or (C) according to the invention preferably comprises at least:

- said extract (a) from 150 to 600 mg, preferably 200 to 300 mg, more preferably 240 to 260 mg, of extract of *Vaccinium macrocarpon* containing at least 10%, more preferably at least 15%, proanthocyanidins (PACs) by weight out of the total weight of (a);
- at least one ingredient or excipient (b) acceptable for pharmaceutical or food use, optionally selected from among cellulose, mannitol, magnesium stearate, magnesium salts of saturated and/or unsaturated fatty acids, silicon dioxide, carboxymethyl cellulose, carboxyethyl cellulose, cross-linked sodium carboxymethyl cellulose and mixtures thereof. Said extract (a) is preferably a dry extract; more preferably still, it is a dry extract of cranberry. The ingredients or excipients (b) acceptable for pharmaceutical or food use are preferably selected from among cellulose, mannitol, silicon dioxide, cross-linked sodium carboxymethyl cellulose and magnesium salts of saturated and/or unsaturated fatty acids.

The composition (CR) as defined above is particularly useful in the treatment and/or prevention of diverticular disease and pathologies linked thereto.

In one embodiment, the present invention provides a composition (C) which comprises, or, alternatively, consists of:

- an extract (a) of a fruit of at least one plant of the genus *Vaccinium* and
- at least one ingredient (b) acceptable for pharmaceutical or food use, said composition being for use in the prevention and/or treatment of diverticular disease or of a pathology deriving from diverticulosis, preferably wherein said use comprises oral administration of (C).

Administration can take place through any route. Preferably, the composition is taken orally, more preferably in the form of pills, capsules, tablets, granular powder, hard-shelled capsules, orally dissolving granules, sachets, lozenges or drinkable vials.

Alternatively, the composition of the invention is formulated as a liquid, for example as a syrup or beverage, or else it is added to food, for example to a yogurt, cheese or fruit juice.

Alternatively, the composition of the invention is formulated in a form capable of exerting an action topically, for example via enema.

Said composition (C) is preferably for use for the treatment or prevention of at least one among diverticular disease, symptomatic uncomplicated diverticular disease (SUDD) and diverticulitis. Said composition (C) is preferably for use in the treatment and/or prevention of diverticulitis.

In a preferred embodiment, the composition (C) for the above-described use is in the form of an oral pharmaceutical preparation, or a dietary supplement or a medical device, comprising a gastro-resistant coating and capable of enabling the release of the extract (a) in the colon.

In a preferred embodiment, in the composition (C) for use as specified above, the extract (a) is from the fruits of at least one plant of the genus *Vaccinium* and the subgenus Oxycoccus, such as *Vaccinium macrocarpon, Vaccinium oxycoccos*, or the subgenus *Vaccinium*, such as *Vaccinium arboreum, Vaccinium crassifolium, Vaccinium boreale, Vaccinium myrtillus* (bilberry) or mixtures thereof.

More preferably, in the composition (C) for use according to the present invention the extract (a) is from the fruits of *Vaccinium macrocarpon* (American cranberry) or *Vaccinium oxycoccos* or a mixture thereof. More preferably still, the extract (a) comprises, or consists of, of the fruits of *Vaccinium macrocarpon*. The extract (a) is preferably a dry extract.

In the composition (C) for use according to the present invention the extract (a) preferably contains at least 10%, more preferably at least 15% or 20% or 30% and no more than 95% or 60% or 40% proanthocyanidins by weight out of the total weight of (a), preferably, but without limitation, A-type proanthocyanidins. Advantageously, the extract (a) is a dry extract; in one embodiment it is a dry extract of cranberry, preferably containing PACs (proanthocyanidins) in a concentration of 5% to 30% by weight or volume, for example 10%, or 15%, or 20%, or 25%.

Proanthocyanidins (PACs) are oligomers and polymers of flavan-3-ols, which belong to the family of the flavonoids and can be quantified, for example, with the "BL-DMAC" method of Prior, R. L. et al. *J. Sci Food Agric* 2010, 90(9), 1473-8, or equivalent methods.

In the context of the present invention the ingredients acceptable for pharmaceutical or food use comprise all the auxiliary substances known to the skilled person for the preparation of forms for oral administration such as, by way of non-limiting example, diluents, absorbents, sweeteners, flavourings, colourants, lubricants, anti-adhesives, glidants, binders, disintegrating agents, surfactants, antimicrobials, antioxidants, stabilisers, thickeners, gelling agents and substances capable of modifying the release of the active ingredient over time of permitting the release thereof only under given physiological conditions, for example in a certain pH interval.

The composition (C) for use as described above, preferably comprises at least:
(a) from 150 to 600 mg, preferably 200 to 300, more preferably 240 to 260 mg, of extract of *Vaccinium macrocarpon* containing at least 10%, more preferably at least 15%, proanthocyanidins by weight out of the total weight of (a);
(b) at least one pharmaceutically acceptable ingredient, optionally selected from among between cellulose, mannitol, magnesium stearate, silicon dioxide, carboxymethyl cellulose and mixtures thereof. More preferably, said composition (C) further comprises a gastroprotective coating, i.e. one that is capable of protecting mixture comprising at least (a) and (b) from the action of gastric juices.

The following examples provide practical embodiments of the invention, there being no intention of limiting the scope and extent thereof.

Preferred forms of compositions (CR) of the present invention are set forth below:
(i) A core comprising:
Cranberry extract containing PACS in a concentration (weight/weight) of 10% or 15% or 30%: from 100 to 500 mg; 150 to 400 mg; 240-300 mg
Cellulose: from 100 to 400 mg; 200 to 350 mg; 300-310 mg
Mannitol: from 1 to 50 mg; 5 to 30 mg; 10-18 mg
Silicon dioxide: from 1 to 50 mg; 3 to 30 mg; 5-8 mg
Cross-linked sodium carboxymethyl cellulose: from 1 to 30 mg; 3 to 20 mg; 5-12 mg
Magnesium salts of fatty acids: from 1 to 30 mg; 3 to 20 mg; 5-10 mg
(ii) a first type of coating (film) of the core (i), comprising the following agents:
a gastro-resistant polymer, such as poly(methyl acrylate-co-methyl methacrylate-co-methacrylic acid) 7:3:1 or another anionic methacrylate copolymer: from 5 to 50 mg; 10 to 35 mg; 18-25 mg
Triethyl citrate E1505: from 0.1 to 5 mg; 0.3 to 3 mg; 0.5-2 mg
Talcum: from 1 to 30 mg; 3 to 20 mg; 5-15 mg; or alternatively,
(ii) a second type of coating (film) of the core (i), comprising the following agents:
Ethyl cellulose: from 5 to 15 mg; 8 to 12 mg; 9.97 mg
Sodium alginate: from 5 to 15 mg; 8 to 12 mg; 9.30 mg
Ammonium hydroxide: from 0.5 to 4 mg; 1.5 to 3 mg; 2.34 mg
Medium-chain triglycerides: from 0.5 to 5 mg; 1.5 to 3 mg; 2.12 mg
Oleic acid: from 0.5 to 3 mg; 1 to 2 mg; 1.17 mg
Purified stearic acid: from 0.01 to 0.5 mg; 0.05 to 0.3 mg; 0.1 mg.

Preferred forms of compositions (CR) of the present invention are set forth below:
(i) A core comprising:
Cranberry extract containing PACS in a concentration (weight/weight) of 10% or 15% or 30%: from 100 to 500 mg; 150 to 400 mg; 240-300 mg
Microcrystalline cellulose: from 100 to 400 mg; 200 to 350 mg; 320-335 mg
Magnesium stearate: from 1 to 30 mg; 2 to 20 mg; 5-10 mg
Silicon dioxide: from 1 to 50 mg; 3 to 30 mg; 5-8 mg
(ii) a first type of coating (film) of the core (i), comprising the following agents:
ethyl cellulose: from 5 to 50 mg; 10 to 30 mg; 15-20 mg;
titanium dioxide: from 0.1 to 15 mg; 0.5 to 10 mg; 1-5 mg
Sodium alginate: from 0.1 to 5 mg; 0.3 to 4 mg; 0.5-2 mg
Oleic acid, stearic acid, Medium-chain triglycerides: each from 0.01 to 3 mg; between 0.05 and 1 mg; or, alternatively,
(ii) a second type of coating (film) of the core (i), comprising the following agents:
Ethyl cellulose: from 5 to 15 mg; 8 to 12 mg; 9.97 mg
Sodium alginate: from 5 to 15 mg; 8 to 12 mg; 9.30 mg
Ammonium hydroxide: from 0.5 to 4 mg; 1.5 to 3 mg; 2.34 mg
Medium-chain triglycerides: from 0.5 to 5 mg; 1.5 to 3 mg; 2.12 mg
Oleic acid: from 0.5 to 3 mg; 1 to 2 mg; 1.17 mg
Purified stearic acid: from 0.01 to 0.5 mg; 0.05 to 0.3 mg; 0.1 mg As a non-limiting example, the composition (CR) according to the present invention can comprise:

EXAMPLE 1

(i) A core comprising:
Cranberry extract containing 15% PACS (weight/weight): 240 mg
Cellulose: 304.4 mg
Mannitol: 15 mg
Silicon dioxide: 5.8 mg
Cross-linked sodium carboxymethyl cellulose: 9 mg
Magnesium salts of fatty acids: 5.8 mg.
Total core 580 mg. Weight range: 575 mg-585 mg
(ii) a coating (film) of the core (i), comprising:
Eudragard® biotic E1207 (Evonik): 20.4 mg
Triethyl citrate E1505: 1 mg
Talcum: 10. 2 mg.
Totale coating/film 31.6 mg. Weight range: 26.1 mg-37.7 mg.
Total coated/film-covered tablet 612 mg. Weight range: 607 mg-617 mg.

EXAMPLE 2

(i) A core comprising:
Cranberry extract containing 15% PACS (weight/weight): 240 mg
Cellulose: 270 mg
Mannitol: 29 mg
Silicon dioxide: 5.8 mg
Cross-linked sodium carboxymethyl cellulose: 29 mg
Magnesium salts of fatty acids: 5.8 mg.
Total core 580 mg. Weight range: 575 mg-585 mg
(ii) a coating (film) of the core (i), comprising:
Ethyl cellulose: 9.97 mg
Sodium alginate: 9.30 mg Ammonium hydroxide: 2.34 mg
Medium-chain triglycerides: 2.12 mg
Oleic acid: 1.17 mg
Purified stearic acid: 0.1 mg.
Total coating/film 25 mg. Weight range: 20 mg-30 mg.
Total coated/film-covered tablet 605 mg. Weight range: 595 mg-615 mg.

Dissolution Test

Materials:
the gastro-coated tablets according to the invention, as per the example, were tested.

Reagents:
Dimethylaminocinnamaldehyde (DMAC, Sigmoid colon code D-4506).
Procyanidin A2 (PCAA2, Sigma, code 28660).
Enzymes and reagents for GID (Sigma).

Methods:
PCA assay according to the spectrophotometric method proposed by Prior et al. (*Multi-laboratory validation of a standard method for quantifying proanthocyanidins in cranberry powders. J. Sci. Food Agric.* (2010), 9, 1473-1478. DOI 10.1002/jsfa.3966).
in vitro GID according to the method proposed by Minekus et al. (*"A standardised static in vitro digestion method suitable for food—an international consensus"* Food Funct. (2014), 6, 1113-1124. DOI 10.1039/C3F060702J).

Results

The tablets were subjected to in vitro GID (in triplicate), with samples taken after 120 min of the gastric phase and after 30, 60, 90 and 120 min of the intestinal phase. The various samples were analysed for PCAA2 content in mg equivalents using the DMAC method and quantified according to the calibration curve shown in FIG. 1 (obtained with the same method as applied to the PCAA2 standard at 640 nm).

The dissolution profile of the tablets according to the present invention is shown in FIG. 2.

Substantially equivalent results were obtained for the gastro-coated tablets of examples 1 and 2.

During the gastric phase of the in vitro GID, there was no analytically verified release of PCA.

The PCA release kinetics (expressed as PCAA2 mg equivalents/tablet, mean of three replicates) during the in vitro intestinal phase is shown in FIG. 2. The release of PCA was analytically observable during the intestinal phase after 60 minutes.

The undigested PCAA2 content of the tablet in mg equivalents was determined after mechanical breakage of the tablet itself and PCA extraction with gastrointestinal fluids and enzymes (GID blank) or with the extraction solvent (acetone/water/acetic acid, 75:24.5:0.5 v/v/v) proposed by Prior et al. (2010). The results obtained were respectively equal to 19.39 and 19.81 PCAA2 mg equivalents/tablet.

Assessment of Effectiveness

For the purpose of assessing the effectiveness of the present invention, in particular as regards the effectiveness of protection of the intestinal mucosa, several in vitro tests were carried out to determine:
  Activity of competition against adhesion of strains of *Escherichia coli*, by blocking of the mechanisms of adhesion, based on analyses of the specific proteins.
  Anti-inflammatory activity through the reduction of the activation of monocytes in macrophages, based on the study of intestinal permeability, assessed as described below:
  Measurement of TEER (trans-epithelial electrical resistance)
  Transepithelial electrical resistance (TEER) is a direct measurement of the functionality of the barrier of epithelial tissues: it reflects global tissue resistance due both to thickness and structure, and represents an indication of the level of integrity of the monolayer and hence of the formation of tight junctions between cells. The transepithelial electrical resistance (expressed in $\Omega cm^2$) is measured using a volt-ohm meter (ERS Millicell).
  Assay with Lucifer Yellow: in the presence of the substance to be evaluated.
  Lucifer yellow is a fluorescent marker impermeable to the cell membrane which enables the integrity of cell junctions to be verified (as a percentage). It is used to study the permeability of a substance on a paracellular level in monocellular layers of Caco-2/Caco goblet cells. The transport of LY is assessed as a passage into the basolateral compartment after a defined period of incubation. The reading of the fluorescent substance is taken by means of a spectrofluorometer with 428 nm excitation and 525 nm emission.

In particular, an assessment will be made of the present invention's effectiveness in protecting the intestinal mucosa following stress induced by *E. coli*, using the experimental model Caco2Goblet®, which is made up not only of intestinal cells, but also of mucus secreting cells, HT29, in co-culture, which is a much more realistic system.

A study was carried out on the protective effectiveness on the intestinal mucosa (CacoGoblet): Colonisation with *E. Coli*.

1. Introduction and Aim of the Study

The biological relevance of the Caco-2 model is well established, since it is an in vitro model of reference used to reproduce the functions of the intestinal mucosa.

CacoGoblet is a model of mucus secreting cells, consisting of permeable seeded supports on microporous polycarbonate filters with human muciparous goblet cells and differentiated and polarised Caco-2 cells.

An experimental model based on the CacoGoblet model was applied for the purpose of assessing the effectiveness of CRANBERRY EXTRACT on behalf of Sofar S.p.A.

The non-cytotoxic concentration was tested at a preliminary stage by MTT assay so as to rule out the potential intrinsic toxicity of the product.

Two protocols were used:
1) Anti-inflammatory Properties of Cranberry Extract in a Co-culture System (THP-1 cells and intestinal epithelial cells)
2) Ability of Cranberries to Prevent Adhesion of *E. Coli* to the Mucosa 2. Experimental Design
1) Anti-inflammatory Properties of Cranberry Extract in an In-vitro Co-culture System (THP-1 cells and intestinal epithelial cells)

The CacoGoblet cells were pre-treated with 10 ng/ml of IL1 beta overnight. Once the IL1 beta had been removed, the intestinal model was treated with cranberry at a non-cytoxic concentration for 24 hours. A parallel treatment was carried out with the reference molecule etacortilen (Dexamethasone Sodium Phosphate) at 0.15% in order to study the overcoming of the inflammatory state of the mucosa.

The products were then removed and the marked THP-1 cells (marked with the cell tracker 5-chloromethyl-fluorescein diacetate) were added to the CacoGoblet cells in the apical compartment and incubated for 1 hour at 37° C.

Once the non-adherent cells had been removed, the residual surface fluorescence of the THP-1 cells was evaluated under a microscope.

The anti-inflammatory activity of the various compounds at the intestinal level was assessed in a static assay using the reduction in the cellular adhesion of THP-1 on CacoGoblet as an endpoint parameter.

2) Ability of Cranberries to Prevent Adhesion of *E. Coli* to Mucosa

CacoGoblet Cells pretreated with Cranberry for 4 hours were colonised with 50 µl of *Escherichia Coli* (ATCC 8739) at 37° C. for 2 hours. At the end of colonisation, the excess bacteria were removed and the following parameters were evaluated:

transepithelial electrical resistance (TEER) and paracellular passage of Lucifer Yellow immunofluorescence of alpha-actinin: Alpha-actinin interacts with Tir, a protein of *E. Coli*, to form the adhesive plaque known as a pedestal, and is a marker of *E. Coli* infection.

ultrastructural analysis of *E. Coli* with a scanning electron microscope (SEM) in order to assess bacterial density and adhesion to the surface of CacoGoblet.

3. Materials 3.1 Experimental System

CacoGoblet™ is a ready-to-use mucus secretion kit for in vitro evaluation of intestinal absorption. The kit consists in permeable supports with 24 wells seeded with human muciparous goblet cells and Caco-2 cells differentiated and polarised in HTS Transwell plates supplemented with an exclusive proprietary transport medium that is stable at room temperature.

The CacoGoblet cell line was supplied at the 20th day of differentiation and used for 5 consecutive days, the complete medium being modified and TEER measured on the basis of an internal procedure. The CacoGoblet™ technical datasheet is appended hereto in Appendix I.

DMEM (lot RNBF5082) containing 10% FBS, 1% glutamine 200 mM and 1% NEAA was used as the medium, as shown in Table 1.

TABLE 1

| NAME AND LOT | CACOGOBLET No. 24 CG 032 112816 | STATUS |
|---|---|---|
| MANUFACTURER | READYCELL | |
| LY % (≤1.4) | 0.51 | Accepted |
| TEER (OHM * CM²) (≥70) | 208.01 | |
| DATE OF ARRIVAL | 15.12.2016 | Accepted |
| DATA OF EXPIRY | 23.12.2016 | |

3.1.1 Culture conditions and use of the experimental system

On receiving the CacoGoblet product, take out the ziplock pouches bags containing the plates. Open the zippers and leave the bag in the dark at room temperature until Friday of the same week. On Friday, incubate the plates at 37° C., with 5% $CO_2$, saturated humidity, for 4 hours. Change the medium and start the experiment the following Monday.

3.2 Substance Under Examination: Identification and Characterisation

The sponsor is responsible for the safety datasheet and characterisation of the substances under examination. (Table 2)

TABLE 2

| PRODUCT NAME | GASTRO-PROTECTED CRANBERRY EXTRACT CONTAINING 15% PACS |
|---|---|
| UNIQUE CODE | CRANBERRY |
| LOT/MANUFACTURER | — |
| | Sofar S.p.A. |
| PRESENTATION | Tablets |
| CONCENTRATION TO BE USED FOR MTT | 10-100-1000 µg/ml |
| CONCENTRATION TO BE USED FOR EFFECTIVENESS STUDY | 1000 µg/ml |
| DOSE | In 300 µl of medium in the apical compartment |
| STORAGE | AT ROOM TEMPERATURE |

3.3 Negative and Positive Control

The NEGATIVE control was the medium on its own.

Positive Control for Protocol 1: Interleukin 1 Beta (SRP6169; lot 9E126460). (Table 3)

TABLE 3

| | PROTOCOL 1 ANTI-INFLAMMATORY AGENT | PROTOCOL 2 COLONISED CONTROL |
|---|---|---|
| NAME | ETACORTILEN 0.15% DEXAMETHASONE SODIUM PHOSPHATE (SIFI, lot 160040) | *Escherichia Coli* (ATCC 8739) Lot number 38/76 |
| UNIQUE CODE | ETACORTILEN | *E. COLI* |
| STORAGE | ROOM TEMPERATURE | −80° C. |
| USE CONCENTRATION | 150 µl of ETACORTILEN + 150 µl of medium | 0.065 OD 600 nm = 1.2 * $10^7$ UFC |
| DOSE | 300 µl | 50 µl |
| TEST CERTIFICATE | | In Appendix I |

4. Methodologies 4.1 *E. coli.*

Strain: *E. COLI* ATCC 8739, lot number.

The strain was inoculated the week before the experiment in a nutrient broth. Furthermore, it was seeded on plates with an agar medium to verify its normal morphology. Then followed incubation at 37° C. for 16-24 hours.

4.1.1 Preparation of suspensions of *Escherichia coli* and colonisation procedure On the day of colonisation, the optical density (OD) at 600 nm of the *E. coli* solution was checked and used for the preparation of the colonisation suspensions based on internal procedures (PM 18).

Bacterial counts were carried out to verify each inoculum in nutrient Agar medium, by seeding the appropriate 10× dilutions on plates (from the undiluted version to the $10^{-7}$ dilution of the suspension of each compartment). The viable bacterial count applied to CacoGoblet corresponds to $1.2*10^7$ CFU.

4.2 Transepithelial Resistance Test (TEER)

4.2.1 Principle

Transepithelial electrical resistance (TEER) is a direct measure of the skin barrier function: it reflects the overall resistance of tissue, due both to its structure and thickness, and measures the integrity of the barrier in terms of tight junctions.

The TEER value of the monolayer of differentiated Caco-2 cells indicates the degree of integrity of the monolayer itself and, accordingly, the formation of tight junctions between the enterocytes. The measurement of TEER (in $\Omega^*cm^2$) is made with a volt-ohm meter (Millicell ERS) (range 200-2000Ω).

4.2.2 Procedure

TEER was evaluated on a monolayer of well-differentiated CacoGoblet cells after 21 days of culture by performing a measurement by insertion using the correct electrode and positioning the short end of the electrode inside the insert, in apical positions (in 0.3 ml of medium). The long end of the electrode was submerged in the well, in a basolateral position (in 0.9 ml of medium).

4.3 Test with Lucifer Yellow 4.3.1 Principle

Lucifer Yellow (LY) is a fluorescent dye impermeable to the cell membrane. It is used to study the paracellular permeability of a substance. When the junctions are intact, Lucifer Yellow has very low permeability; if, on the other hand, the junctions are damaged, the flow of Lucifer Yellow is greater. Therefore, this test makes it possible to verify the integrity of the cell junctions in the presence of the substance to be examined.

4.3.2 Procedure

Lucifer Yellow (LY) is applied in the apical compartment at a concentration of 100 μM, following exposure to the substance to be examined, dissolved in saline solution (0.25 ml). 0.70 ml of saline solution is added in the basolateral compartment. The transport of LY is evaluated in terms of the passage from the apical compartment to the basolateral compartment after a defined period of incubation of 1 hour at 37° C.

The reading is taken by means of a spectrofluorometer (TECAN INFINITE M200) with 428 nm excitation and 525 nm emission.

The percentage of permeability is calculated by means of the following formula:

LY Flow=$(RFU_{BL}/RFU_{AP}\text{initial}) \times 100$

In an intact CacoGoblet monolayer the LY flow should be less than 1.4%.

4.4 Scanning Electron Microscope (SEM)

The samples to be examined by SEM were fixed with a 2.5% glutaraldehyde solution in 0.1 M PBS for 24 hours, washed in 0.1 M sodium cacodylate buffer, pH 7.4, and extracted in 1% osmium tetroxide (OsO4) in the same sample (2 hours at room temperature). The samples were then dehydrated in ascending degrees of ethanol at room temperature and hexamethyldisilazane overnight.

The samples were placed on pins with carbon tabs and coated with a layer of gold using the SEM E5100 metal coater by Polaron Equipment Limited, then transferred to the Zeiss Sigmoid colon electron scanning microscope for viewing and photographs.

SEM Sample Generated During the Study (Table 4)

TABLE 4

| VS 79-16 end-point | SAMPLE CODE |
|---|---|
| SEM | NC 6H-6 |
|  | E. COLI 2H-6 |
|  | PR (4 h) + E. COLI 2H-6 |

4.5 Immunofluorescence: Alpha-Actinin 4.5.1 Principle

Immunofluorescence marking is a histological technique for detecting specific structures or molecules in cellular compartments of histological sections. The technique is based on the specificity of the antibody binding the antigen for the detection of the target molecule and a system of detection by means of a fluorescence microscope, using an indirect method: a primary antibody capable of specifically recognising the target and a secondary antibody bound to the fluorophore, capable of recognising the primary antibody.

4.5.2 Procedure

After fixing in cold ethanol for 30 minutes and in cold acetone for 3 minutes, the intestinal mucosa was washed with PBS and the non-specific reactions were blocked with 1% BSA in PBS for 30 minutes. Each insert was incubated overnight at 4° C. with alpha actinin antibody (monoclonal mouse antibody, ab18061, lot GR256204-1) at 1 μg/ml in 1% BSA in PBS. After washing, the tissues were incubated at room temperature for 1 hour with the secondary antibody (goat anti-mouse antibody Alexa Fluor 488, Invitrogen A10-680) 1:400 in 1% BSA in PBS. After washing, the nuclei were stained with DAPI and analysed under a Leica DM 2500 fluorescence microscope.

4.6 Monocyte-Epithelial Cell Adhesion Assay 4.6.1 Principle

The CacoGoblet cells were treated overnight with IL-1beta, the pro-inflammatory cytokine, prior to the adhesion assay in order to create inflamed mucosa. The treated monolayers were then treated with the products for 24 hours. The marked THP-1 cells were added on top of the CacoGoblet in each well. The THP-1 cells were marked with the fluorescent dye chloromethylfluorescein diacetate (CMFDA; Invitrogen). After incubation, the monolayer was gently washed to remove the non-adherent THP-1 cells. The adherent cells marked with the fluorescent dye were viewed under a fluorescence microscope.

4.6.2 Procedure

Once treated, the marked THP-1 cells were applied on top of the CacoGoblet.

The THP-1 cells were marked with the fluorescent dye chloromethylfluorescein diacetate (CMFDA Exc. 492, Em 517; Invitrogen).

After 1 hour of incubation, the monolayer was gently washed to remove the non-adherent THP-1 cells.

The adherent cells marked with the fluorescent dye were viewed under a fluorescence microscope.

5. Results 5.1 Cell Viability via the MTT Test

Figure 3:
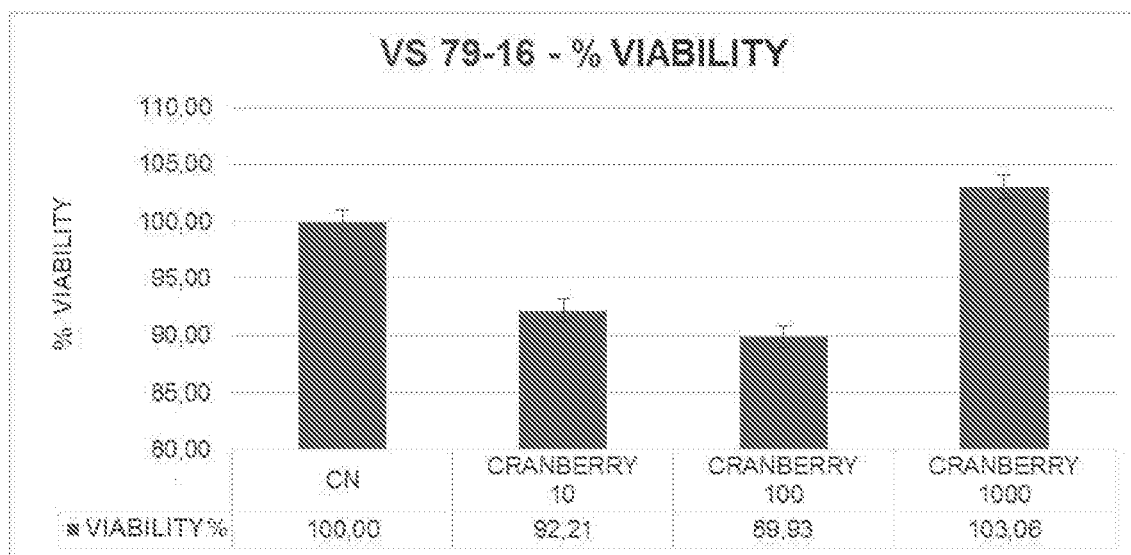
FIG. 3 depicts cell viability after 24 hours of treatment with cranberry at 10-100-1000 µg/ml.

The results of the MTT test are presented in FIG. 3. FIG. 3 shows cell viability after 24 hours of treatment with cranberry at 10-100-1000 μg/ml.

The negative control (medium on its own) was assigned a viability of 100%.

At all of the concentrations tested, the products did not reduce viability compared to the negative control.

The non-cytotoxic concentration selected for the study of effectiveness was 1000 μg/ml. At this concentration, the interference of the substance examined with the MTT test was 32%.

Anti-inflammatory Properties of Cranberry Extract in an In-vitro Co-culture System (THP-1 cells and intestinal epithelial cells)

5.2 Monocyte-epithelial Cell Adhesion Assay

Once treated, the marked THP-1 cells were applied on top of the CacoGoblet.

After 1 hour of incubation, the monolayer was gently washed to remove the non-adherent THP-1 cells. The adherent cells marked with the fluorescent dye were viewed under a fluorescence microscope; the results are presented in FIG. 4.

Figure 4:
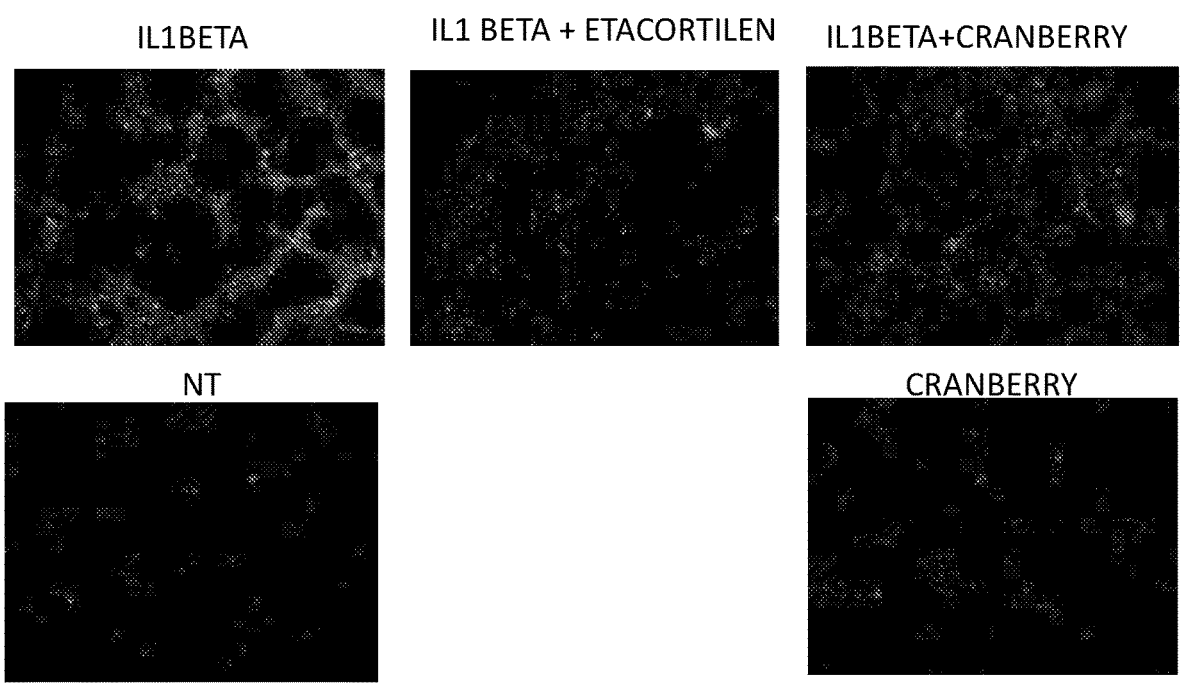
FIG. 4 depicts monocyte-epithelial cell adhesion in untreated inflamed CacoGoblet.

FIG. 4 shows monocyte-epithelial cell adhesion in untreated inflamed CacoGoblet

As expected, following the treatment with IL1beta an increase in the adhesion of the THP-1 cells was observed.

As expected, a very small number of THP-1 cells showed to be adherent to the CacoGoblet epithelium (negative control, NT).

CRANBERRY ON ITS OWN, on healthy mucosa, reduced the adhesion of THP-1 cells.

A significant decrease in the adhesion of THP-1 cells was observed following the application of etacortilen on the inflamed mucosa.

A significant decrease in the adhesion of THP-1 cells was observed following the application of CRANBERRY on the inflamed mucosa, slightly smaller than after the treatment with etacortilen.

Ability of Cranberry to Prevent Adhesion of E. Coli to Mucosa 5.3 Measurement of TEER FIG. 5 shows the results of the trans-epithelial electrical resistance (TEER) expressed in ohm*cm$^2$ at basal (0 hours), after 4 hours of treatment with the products and after 2 hours of colonisation by E. coli (6 hours of treatment altogether).

The TEER values before the treatment (T=0 hours) indicate the overall resistance of the barrier correlated to the integrity of the structure of the tight junctions.

TEER, a physical parameter of the integrity of the barrier of the mucosa, was used to characterise the influence of the product on the paracellular flow of ions at the level of the mucosal epithelium.

Figure 5:
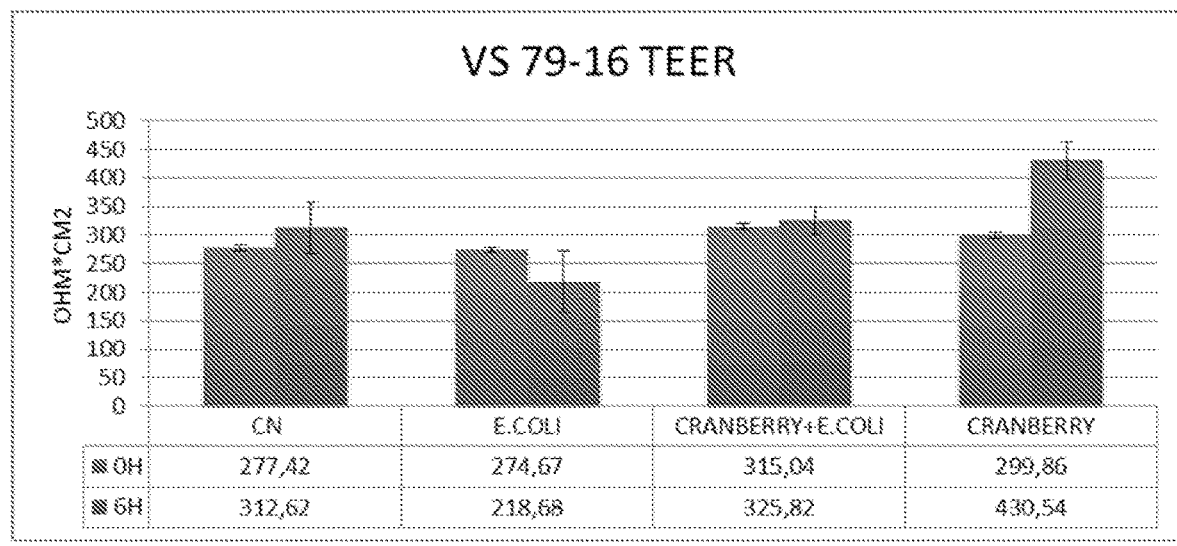
FIG. 5 depicts the results of the trans-epithelial electrical resistance (TEER) expressed in ohm * $cm^2$ at basal (0 hours), after 4 hours of treatment with the products and after 2 hours of colonization by E. coli (6 hours of treatment altogether).

FIG. 5 shows the trans-epithelial electrical resistance (TEER) expressed in OHM*cm$^2$ at basal (0 hours), after 4 hours of treatment with cranberry 1000 μg/ml on its own or after 2 hours of colonisation by E. Coli. 6 hours was the overall culture time of the negative control.

As indicated in FIG. 5, the colonisation by E. coli caused a reduction in TEER from 274.67 ohm*cm$^2$ to 218.68 ohm*cm$^2$ after 2 hours of treatment (−21%).

The 4-hour pretreatment with cranberry caused an increase in TEER from 315 ohm*cm$^2$ to 325.82 ohm*cm$^2$ and countered the adhesion of E. coli (3% recovery of TEER).

After 4 hours of treatment, cranberry on its own induced a 43% increase in the TEER values (from 299.86 ohm* cm$^2$ to 430.54 ohm*cm$^2$): these results indicate the valid properties of film formation and the positive effectiveness of the cranberry extract on the epithelial barrier in both the presence and absence of E. coli.

5.4 Test with Lucifer Yellow: Paracellular Permeability

Figure 6:
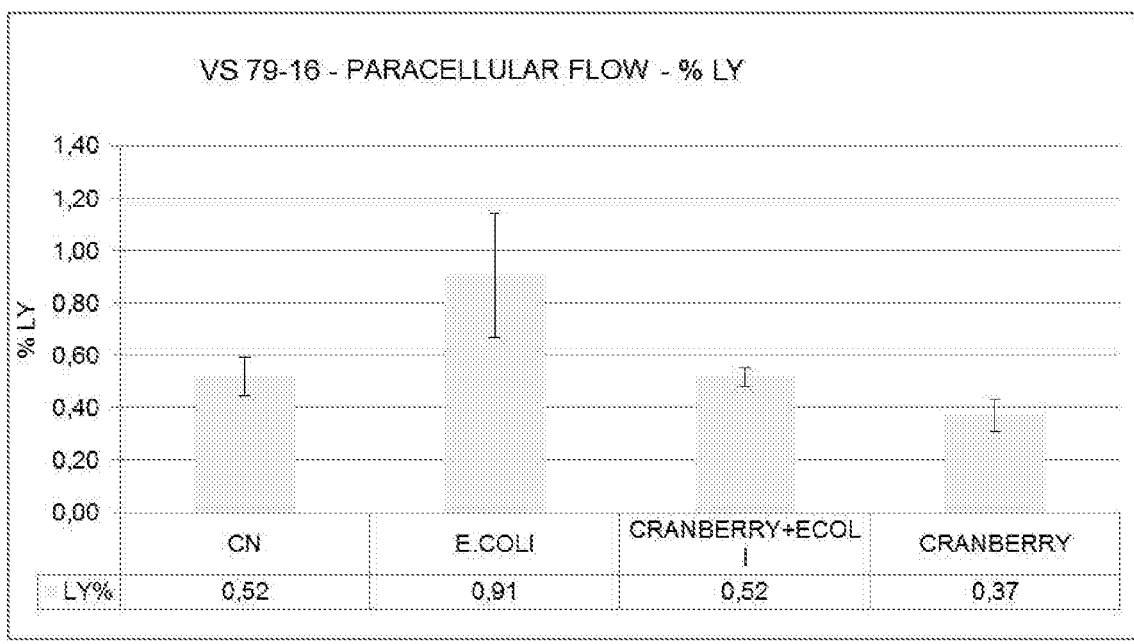
FIG. 6 depicts the flow of Lucifer Yellow (LY) after 6 hours of treatment (4 hours with cranberry and 2 hours of colonization by E. coli) as compared to LY at time zero in the apical compartment.

The paracellular flow of Lucifer Yellow (LY) was evaluated at the end of the period of exposure; the results of the fluorescence measurement are shown in FIG. 6.

FIG. 6 shows the % flow of LY compared to LY at time zero in the apical compartment. FIG. 6 shows the flow of LY after 6 hours of treatment (4 hours with cranberry and 2 hours of colonisation by E. coli).

The negative control (NC) had 0.52% permeability to LY. E. coli had greater permeability to LY (0.91%) than the negative control (74% increase in the passage of LY versus NC).

No significant difference emerged between the negative control and the tested product: the pretreatment with Cranberry restored the intestinal epithelium and prevented adhesion by E. coli.

Cranberry on its own has protective effectiveness: a 29% reduction in the passage of LY compared to the negative control was observed.

5.5 Immunofluorescence Staining of Alpha-actinin

The series of images below show the samples analysed under a fluorescence microscope. The green colour represents the protein alpha-actinin located at the level of the membrane. Alpha-actinin interacts with Tir, a protein of E. Coli, to form the adhesive plaque known as a pedestal, and is a marker of E. Coli infection.

Figure 7:
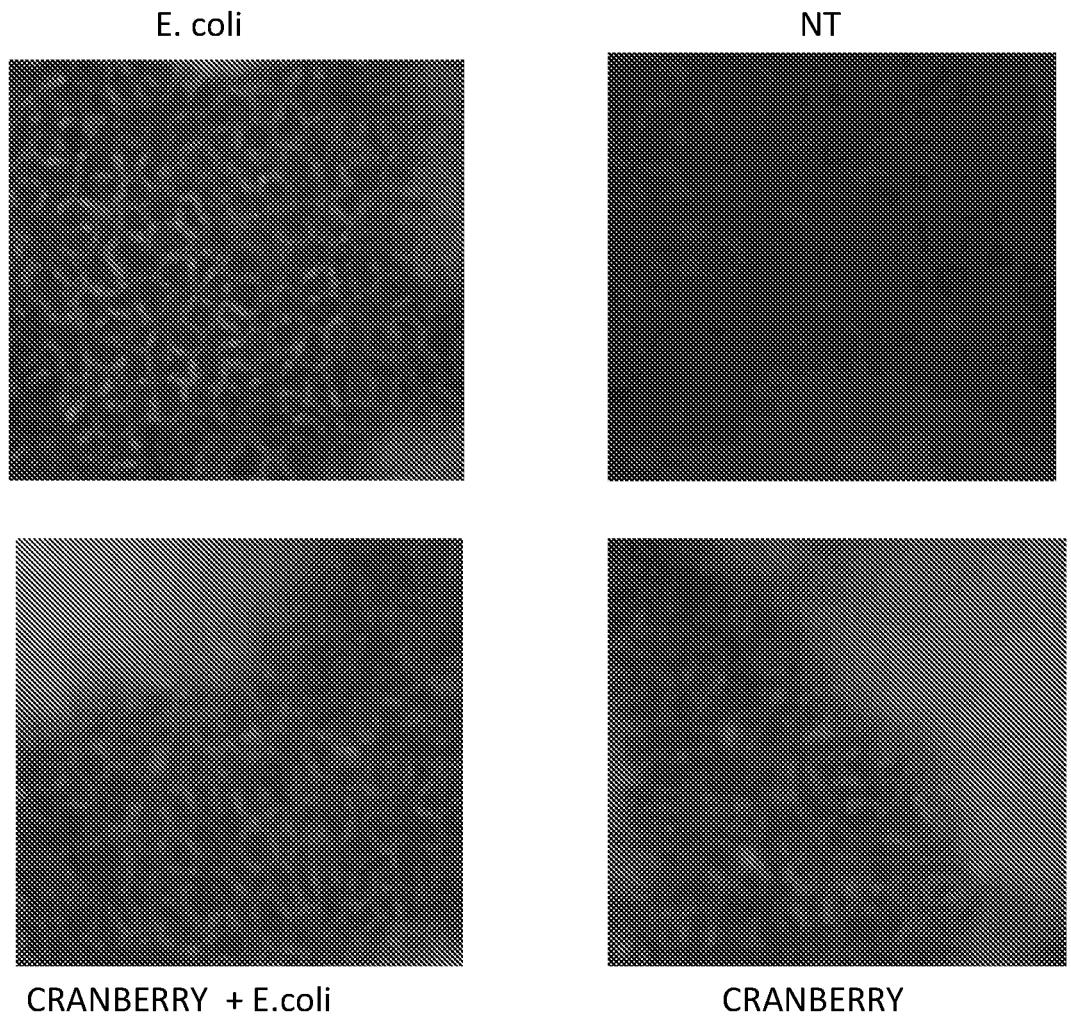
FIG. 7 depicts the immunofluorescence of alpha-actinin in samples colonized by Escherichia coli and treated or not treated with Cranberry.

FIG. 7 shows the immunofluorescence of alpha-actinin in samples colonised by Escherichia Coli and treated or not treated with Cranberry.

The increase in the fluorescent colour at the level of the membrane is evident after colonisation by E. coli compared to the negative control.

Cranberry induced a slight decrease in alpha-actinin when it was applied on its own or as a pretreatment prior to colonisation by E. coli (non-significant difference compared to colonisation by E. Coli).

5.6 Scanning Electron Microscope

Figure 8:
FIG. 8 depicts ultrastructural images of Caco-2 cell microvilli drawn from the literature.
Figure 8:
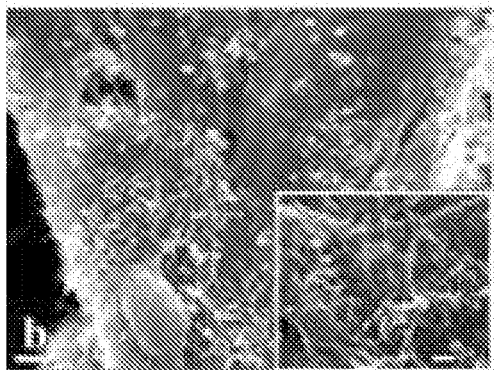
Figure 8:
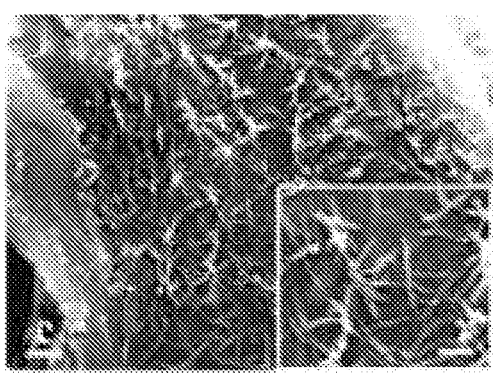
Figure 8:
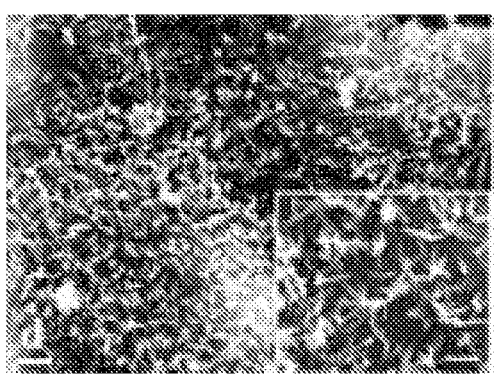
Figure 8:
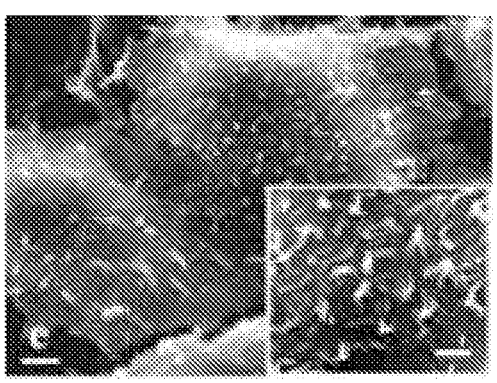
Figure 8:

FIG. 8 shows ultrastructural images of Caco-2 cell microvilli drawn from the literature. (BCD Cancer 2008 8:227)

In the untreated Caco-2 cells a large number of microvilli can be observed. The cell margins do not appear. Insert: long microvilli are present. b. Cells treated with EGF. Numerous vesicles are evident. Insert: a reduced number of microvilli are present. c-f: treated cells. The microvilli decrease in number and lose their erect position.

Historical VitroScreen data on the colonisation of Caco-2 cells by E. coli: The proliferation and adhesion of E. coli to the cell layer are evident (red arrow).

Figure 9A:
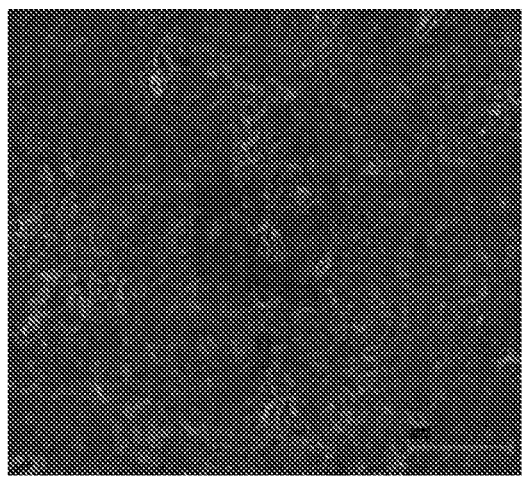
FIGS. 9A and 9B depict the samples analyzed under a scanning electron microscope.
Figure 9B:
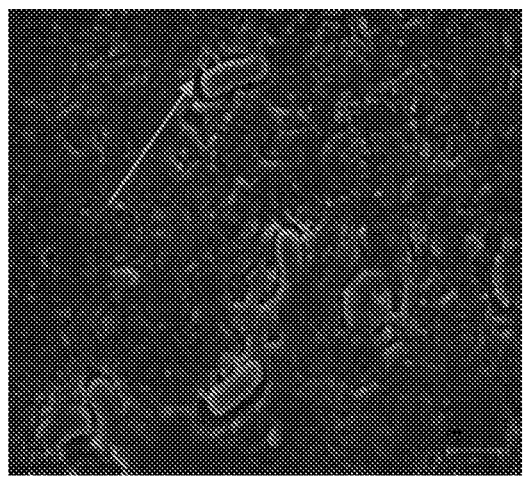

FIGS. 9A and 9B show the samples analysed under a scanning electron microscope.

Figure 10A:
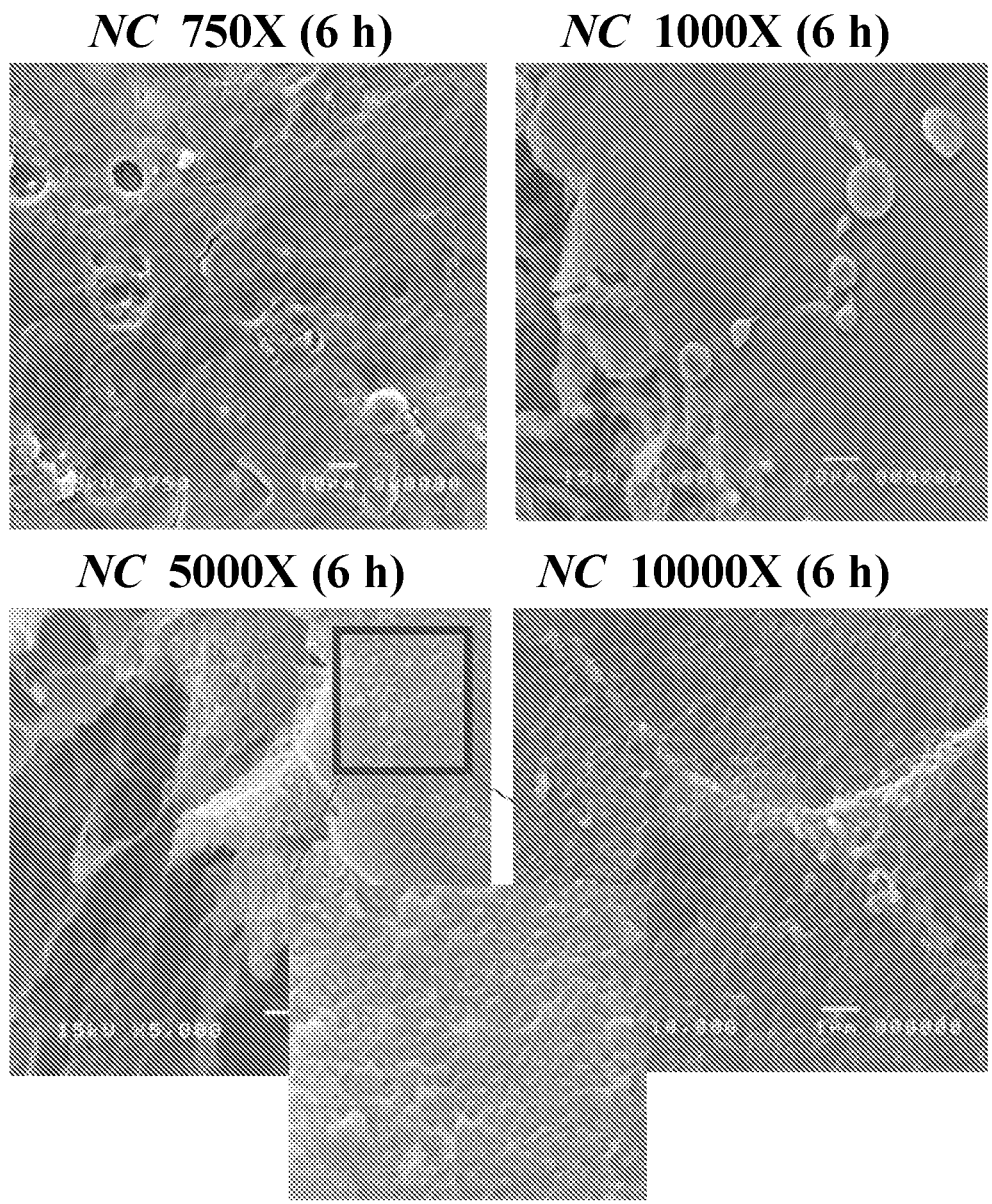
FIG. 10A depicts untreated CacoGoblet at 6 hours.

FIG. 10A shows the negative control: untreated CacoGoblet at 6 hours

As expected, the negative control showed no cellular stress or bacterial contamination. The tissue was trophic, with well-structured desmosomes (1000×). The microvilli appear to be well organised over the entire surface: a dense brush-like border of microvilli can be observed (5000×, red box).

Figure 10B:
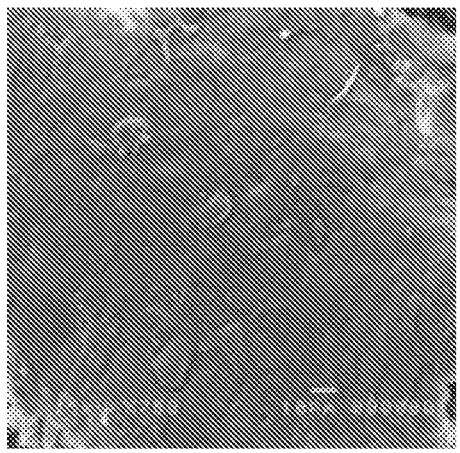
FIG. 10B depicts the colonization of the tissue by E. coli at 2 hours.
Figure 10B:
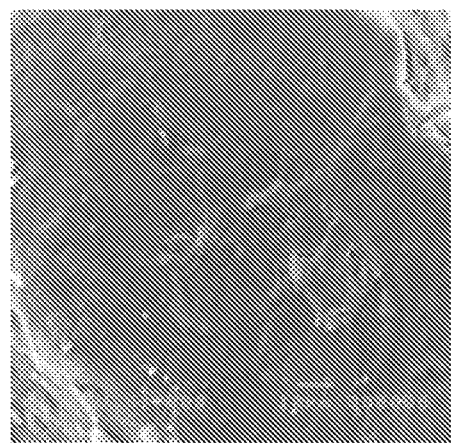
Figure 10B:
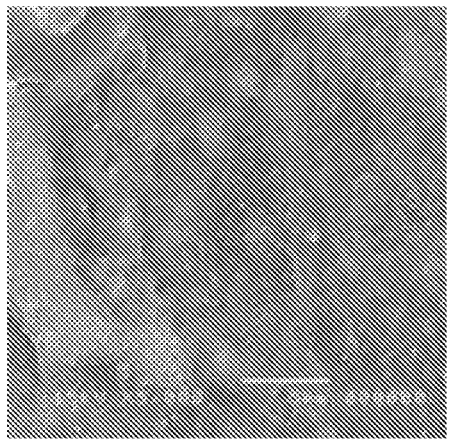
Figure 10B:
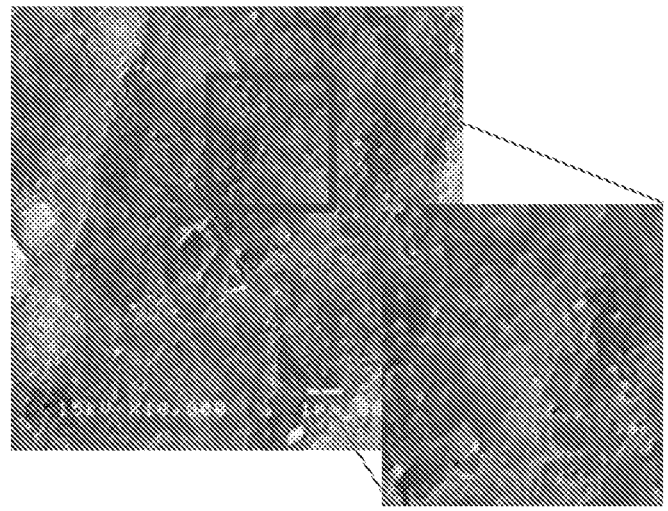

FIG. 10B shows the colonisation of the tissue by E. coli, 2 hours

Because of the solution of technical problems, no proliferation of E. coli is present on the surface of the CacoGoblet. However, the monolayer shows microvilli damaged on the surface; they are fewer in number and have lost their normal position (10000×, red box) compared to the negative control, which indicates that E. coli caused damage to the brush-like border.

Figure 10C:
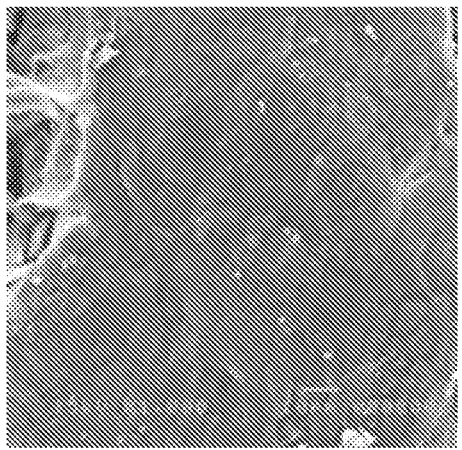
FIG. 10C depicts the pre-treatment with Cranberry for 4 hours prior to colonization by E. coli for 2 hours.
Figure 10C:
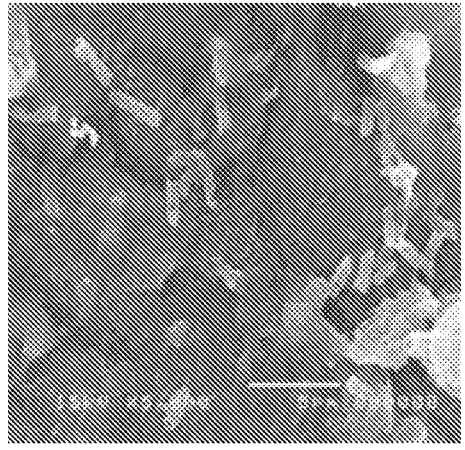
Figure 10C:
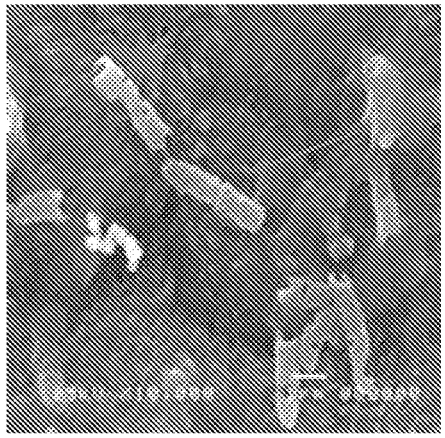

FIG. 10C shows the pretreatment with CRANBERRY for 4 hours prior to colonisation by E. coli for 2 hours.

The monolayer appears to be well structured and shows microvilli on the surface (5000×). Few E. coli cells are visible and their morphology is altered (10000×, red arrow), with clear signs of lysis. In addition, abundant bacterial debris (10000×, red star) is evident, indicating that the treatment with Cranberry caused damage to E. coli.

6. Conclusions

Various experimental models based on in-vitro CacoGoblet intestinal epithelium were applied in order to assess the effectiveness of CRANBERRY EXTRACT on behalf of Sofar S.p.A.

The non-cytotoxic concentration was tested at a preliminary stage via MTT assay so as to rule out the potential intrinsic toxicity of the product.

The highest non-cytotoxic concentration selected for the effectiveness study was 1000 µg/ml.

Two protocols were used:
1) Anti-inflammatory Properties Of Cranberry Extract In A Co-culture System (THP-1 cells and intestinal epithelial cells)
2) Ability Of Cranberry to Prevent Adhesion of *E. Coli*

The following parameters were evaluated in order to arrive at a conclusion regarding:
Monocyte-epithelial cell adhesion in CacoGoblet with inflammation induced by IL1-beta (anti-inflammatory effectiveness)
Trans-epithelial electrical resistance (TEER) and paracellular flow of LY (alteration of the epithelial barrier)
Ultrastructural analysis of *E. Coli* with a scanning electron microscope (SEM) (countering of the adhesion and proliferation of *E. coli*)
location of alpha-actinin by immunofluorescence (countering of the adhesion of *E. coli*)

In conclusion, the results demonstrated that:
1) CRANBERRY, applied on an inflamed intestinal mucosa, induced a significant reduction in adhesion to THP-1 cells, suggesting a significant anti-inflammatory action.
2) Pretreatment with Cranberry for 4 hours slightly countered the damage of the barrier induced by the adhesion of *E. coli*; Cranberry on its own, after 4 hours of treatment, induced a 43% increase in the TEER values, suggesting an excellent film forming ability.
3) Cranberry on its own performs a protective action on the integrity of the barrier: a 29% reduction in the passage of LY was observed compared to the negative control. No significant difference emerged with the tested product compared to the negative control: the pretreatment with Cranberry restored the intestinal epithelium and prevented adhesion by *E. coli*.
4) The staining with α-actinin, which is relevant as a biomarker for the adhesion of *E. coli*, was not altered to a significant degree by the treatment with Cranberry under the experimental conditions adopted; however, a slight reduction in fluorescence was observed.
5) The analysis by scanning electron microscopy revealed a direct activity of Cranberry against the adhesion, viability and morphology of *E. coli*.

The invention claimed is:

1. A tablet or capsule consisting essentially of an extract selected from the group consisting of *Vaccinium macrocarpon, Vaccinium oxycoccos, Vaccinium arboretum, Vaccinium crassifolium, Vaccinium boreale* and *Vaccinium myrtillus*; ethyl cellulose; sodium alginate; purified stearic acid; and ammonium hydroxide.

2. The tablet or capsule of claim 1, wherein said extract is dry and is present in an amount of from 150 mg to 600 mg.

3. The tablet or capsule of claim 1, wherein said extract is present in an amount of from 200 mg to 300 mg, and wherein said extract is 80% to 99% proanthocyanidins by weight, relative to the total weight of said extract.

4. The tablet or capsule of claim 1, wherein said extract is a dry extract of cranberry, and wherein said extract is 5% to 30% proanthocyanidins by weight or volume.

5. The tablet or capsule of claim 1, wherein the ethyl cellulose, sodium alginate, purified stearic acid, and ammonium hydroxide form a gastro-resistant layer around the extract.

6. The tablet or capsule of claim 5, wherein said gastro-resistant layer breaks down and dissolves from a pH value of about pH 7.0 to about pH 7.5.

7. The tablet or capsule of claim 1, wherein ethyl cellulose is present in an amount from 5 mg to 15 mg; from 8 mg to 12 mg; or 9.97 mg;
sodium alginate is present in an amount from 5 mg to 15 mg; from 8 mg to 12 mg; or 9.30 mg; ammonium hydroxide is present in an amount from 0.5 mg to 4 mg; from 1.5 mg to 3 mg; or 2.34 mg; and purified stearic acid is present in an amount from 0.01 mg to 0.5 mg; from 0.05 mg to 0.3 mg; or 0.1 mg.

8. The tablet or capsule of claim 4, wherein said proanthocyanidins are in a concentration of 10%, 15%, 20%, or 25% by weight or volume.

9. The tablet or capsule of claim 6, wherein said gastro-resistant layer breaks down and dissolves from a pH value of about 6.5 to a pH value of about 8.

10. The tablet or capsule of claim 6, wherein said gastro-resistant layer breaks down and dissolves in a time from 30 minutes to 120 minutes or from 45 minutes to 90 minutes.

11. The tablet or capsule of claim 7, wherein the ethyl cellulose is in an amount of about 9.97 mg; sodium alginate is in an amount of about 9.30 mg; ammonium hydroxide is in an amount of about 2.34 mg; and the purified stearic acid is in an amount of about 0.1 mg.

* * * * *